(12) United States Patent
Baugh et al.

(10) Patent No.: US 6,656,919 B1
(45) Date of Patent: Dec. 2, 2003

(54) METHOD AND A PRODUCT FOR THE RAPID DECONTAMINATION AND STERILIZATION OF BACTERIAL ENDOSPORES

(76) Inventors: Clarence L. Baugh, 2084 Deer Creek Country Club Blvd., Deerfield Beach, FL (US) 33442; Thomas E. Baugh, 8585 Boca Rio Dr., Boca Raton, FL (US) 33433; Charles L. Baugh, 21404 S. 54 th. Dr., Boca Raton, FL (US) 33486

( * ) Notice: Subject to any disclaimer, the term of this patent is extended or adjusted under 35 U.S.C. 154(b) by 14 days.

(21) Appl. No.: 10/042,246

(22) Filed: Jan. 11, 2002

(51) Int. Cl.[7] .................. A61K 31/70; A61K 31/14; A61K 31/11; A61K 31/045
(52) U.S. Cl. .................. 514/46; 514/2; 514/642; 514/693; 514/728; 514/724
(58) Field of Search .................. 514/2, 642, 693, 514/728, 724, 46

(56) References Cited

U.S. PATENT DOCUMENTS

| 4,656,038 A | * | 4/1987 | Baugh .................. 424/164 |
| 5,800,821 A | | 9/1998 | Acheson et al. |
| 5,998,691 A | | 12/1999 | Abel et al. |
| 6,057,488 A | | 5/2000 | Koper et al. |
| 6,132,356 A | | 10/2000 | Schabdach et al. |
| 6,267,966 B1 | | 7/2001 | Baillie |
| 6,280,601 B1 | | 8/2001 | Doring |
| 6,293,861 B1 | | 9/2001 | Berry |
| 6,296,808 B1 | | 10/2001 | Pearman |

OTHER PUBLICATIONS

Tawarantani et al., "Resistance of cation–exchanged *Bacillus subtilis* var. niger spores to antibacterial agents and their germination property", Bokin Bovai (1987), 15(6), p. 273–280 (cpopy of abstract).*

Trujillo et al., "Sporostatic and sporocidal properties of aqueous formaldehyde", Appl. Microbiol. (1972), 23(3), pp. 618–622 (copy of abstract).*

\* cited by examiner

*Primary Examiner*—Kevin E. Weddington
(74) *Attorney, Agent, or Firm*—C. J. Husar Esq.

(57) ABSTRACT

The present invention is directed to a method for the disinfection and sterilization of material and surfaces contaminated with one or more members selected from the group consisting of bacteria and bacterial spores, comprising the steps of: (a) providing a biocidal fluid containing a mixture of effective amounts of a germinant and a germicide; and (b) contacting the material and surfaces contaminated with one or more members selected from the group consisting of bacteria and bacterial spores, with the biocidal fluid of step (a) for a time sufficient for disinfecting and sterilizing said material. The invention also provides a sterilizing composition suitable for killing and rendering spores lifeless comprising: (a) an effective amount of a germinating agent; (b) an effective amount of a germicide.

15 Claims, No Drawings

METHOD AND A PRODUCT FOR THE RAPID DECONTAMINATION AND STERILIZATION OF BACTERIAL ENDOSPORES

FIELD OF INVENTION

The present invention relates to methods and compositions for killing or rendering lifeless sporular forms of microbes. More particularly, the present invention relates to methods and compositions for killing or rendering lifeless sporular forms of *Bacillus anthracis*. This invention also relates to a broad-spectrum biocidal composition effective for the rapid killing of a wide variety of bacteria and spores on a wide variety of nonabsorbent surfaces such as metals, plastics, resins, woods, rubbers, ceramics, and glasses.

The methods of the present invention are highly effective and include using a composition that is capable of inactivating (killing) micro-organisms including bacterial and fungal spores at room temperature such that the initial count is reduced to zero in EPA-specified tests (AOAC Manual for Sporicidal Testing, Chapter 14) involving *Bacillus subtilis, Bacillus cereus, Bacillus anthracis, Clostridium sporogenes, Pseudomonas aeruginosa* and *Staphyloccus aureus*.

This invention also relates generally to compositions for disinfecting and sterilizing substrates as well as to processes for preparing and using such compositions.

This invention relates to aqueous chemical compositions for room temperature sterilization with improved effectiveness and longer active life. In use, the composition of the present invention can also be employed as a cleaner, sanitizer, disinfectant, and chemical sterilizer. The numerous advantages of this invention with respect to its methods of use and applications are further described below.

BACKGROUND OF INVENTION

The threat of terrorist action using chemical warfare (CW), biological warfare (BW), chemical or infectious agents has occurred throughout the world and more recently a terrorist attack occurred in the United States wherein anthrax spores were disseminated through the mail system. These acts of terrorism are unpredictable and counter efforts have been aimed at rapid, accurate diagnosis and speedy treatment.

Additionally, the recent demise of the cold war and a decline in super-nation tensions has been accompanied by an increase in concern about the viability of weapons of mass destruction such as chemical and biological (CB) weapons. CB weapons include chemical agents such as phosgene, nerve agents such as Sarin, and biological agents such as anthrax or smallpox. CB weapons may be delivered to occupants within a building by releasing the agents either external to the building or within the building.

Anthrax is a highly toxic biological warfare agent. Anthrax is a natural disease of herbivorous animals that can be transmitted to humans. The causative agent *Bacillus anthracis*, can form spores which are extremely hardy and can remain alive for a very long time. After inhalation of a heavy dose of anthrax spores, however, the onset of the disease may occur within a day and death may follow rapidly in a couple of days.

*Bacillus anthracis* is the etiologic agent responsible for anthrax, a disease often found in persons exposed to infected animals or their products. Persons particularly exposed to animals include veterinarians, laboratory technicians, ranchers and employees working with skin or hair of animals. The mode of entry into the body may be the skin or, when contaminated meat is eaten, the gastrointestinal tract. Inhaling of spores can cause inhalation anthrax, a disease that can be fatal.

In response to such a release of harmful agents, people may be moved into a building, out of a building, or from one part of a building to another, depending on the location of the release and the relative safety of various areas of the building or buildings.

In response to such an agent release, it may also be desirable to attempt to wash the harmful agent from people to benefit the contaminated personnel and to lessen the spread of the agent carried by the contaminated personnel. While such decontamination may be desirable, it may not be desirable to generate concern by having an explicit and distinct CB decontamination station placed in a building hallway.

The risk of CB weapons being used may escalate rapidly over a short time period. Given long-range awareness and time for preparation, particular buildings such as key military sites, can be equipped or designed in advance to deal with this possibility. However, the awareness of the imminent likely use of CB weapons against a building may give only a short time period for preparation. Also, the risk against a particular building may increase in a short time period.

What would be desirable is a system for decontaminating people that is unobtrusive and does not call attention to itself as a decontamination station for CB warfare. What would be desirable is a system for CB decontamination that could be added relatively quickly to existing building utilities while attracting little attention and incurring little expense.

Spores are known to form from aerobic Bacilli, anaerobic Clostridia, selected sarcinae and a few actinomycetes. Spores resemble certain plant seeds in that they do not carry out any metabolic reactions. In this regard they are especially suited to withstand severe environmental stress and are known to survive prolonged exposures to heat, drying, radiation and toxic chemicals. These properties make spores especially difficult to kill in environments, like living tissue or objects which come in contact with living tissue, which would be adversely effected by extreme conditions. Additionaly, it is also known that spores are metabolic by-products in the life cycle of some bacteria and fungi, and are often very resistant to physical and chemical disinfectant agents. Spores contain one or several nuclei. Fungi produce a variety of exospores, including conidia, chlamydospores (thick-walled and very resistant), and sporangiospores. Bacteria produce endospores, i.e. spores located within the cytoplasm of the parental cell.

Bacterial endospores are differentiated cells formed within a vegetative cell; they encase a genome in an insulating dehydrated vehicle that makes the cell ametabolic and resistant to various lethal agents, but permits subsequent germination in an appropriate medium. Spores are much more resistant than the parental (vegetative) cell to the lethal effect of heat, drying, freezing, toxic chemical s and electromagnetic radiations. Spores are formed by the invagination of a double layer of the cytoplasmic membrane, which closes off to surround a bacterial chromosome and a small amount of cytoplasm. A thin spore wall, and a thicker cortex with a much looser peptidoglycan, are synthesized between the two layers; outside the cortex is a protein coat, rich in disulfide cross-links and constituting up to 80% of the total protein of the spore. The keratin-like impervious properties of the coat account for the resistance to attack by deleterious chemicals, while the dehydration and the presence of a large amount of Calcium and dipicolinate contribute to the heat resistance.

It is known that disulfide bridges are a feature of cellular walls and other protein-containing features of bacterial cells. Mahler, H. & Coredes, E., Structural Organization of Proteins, Biological Chemistry 74 (1966). A typical bacterial spore is surrounded by an exosporium, a loose sac peculiar to some spore species. Other layers, working inwardly, include (a) multi-layered coats containing proteins rich in disulfide linkages, (b) a thick cortex layer which contains the polymer murein (or peptidoglycan), (c) a plasma membrane, and (d) a core or spore protoplasm.

A bacterial spore's first line of resistance to exogenous agents consists of the proteinaceous outer coats that contain keratin-like proteins. As is well-known, the stability of keratin structures is due to frequent primary valence cross links (disulfide bonds) and secondary valence cross links (hydrogen bonds) between neighboring polypeptide chains. Keratin-like proteins are typically insoluble in aqueous salt solutions or dilute acid or base solutions, and are also resistant to proteolytic enzymes and hydrolysis. In other words, the layered outer coats are rather inert and play a predominant role in protecting the spore against exogenous agents.

The outer layers are coats of an alkali soluble protein that tends to form fibrils in vitro. This alkali soluble layer can be removed only after mechanical rupture of the spores or treatment with a reagent that breaks disulfide bonds, such as mercaptoethanol. It has been speculated that a disulfide-rich layer holds the alkali soluble layer within the spore in some manner (the physical structure of disulfide bridges for instance could be the integral part of that cell layer function).

Penetration of the outer layers seems to play an important role in cidal action of spores. Physical or chemical modifications to the cell wall allow diffusion of anti-microbial agents into the protoplasm, thereby interrupting cellular metabolism and DNA synthesis.

The protective outer layers of bacterial vegetative cells are more susceptible to antimicrobial agents than are spores, thus an agent capable of disrupting spore cell walls and penetrating the inner layers of a spore is expected to kill vegetative cells also.

A striking feature of spores is their huge content of $Ca^{++}$, for which active transport units appear in the membrane of the mother cell early during sporulation. Normally the $Ca^{++}$ is accompanied by a roughly equivalent amount of dipicolinic acid, which can chelate $Ca^{++}$; dipicolinate is almost unique to bacterial spores and may constitute as much as 15% of their weight. Dehydration and ionic conditions are undoubtedly major factors in stabilizing spore proteins. Ca dipicolinate evidently plays a large role, by some as yet unknown mechanism, for its content markedly influences heat resistance. Recent research results point out to the control of calcium flow across the cytoplasmic membrane, thanks to a "calcium pump" assembly embedded into the bi-layer lipid membrane of cells and defining a calcium selective through-membrane channel ("The Cycling of Calcium as an Intracellular messenger", Scientific American, October 1989).

Fungi, viruses and vegetative cells of pathogenic bacteria are sterilized within minutes at 70 degrees centigrade; many spores are sterilized at 100° C. However, bacterial endospores can survive boiling for hours. Heat is presently the most commonly used means to insure sterilization of spores.

The outer coat of spores is made of a keratin-like protein which comprises as much as 80% of the total protein of the spore. It is this protein coat which is responsible for the resistance of spores to chemical sterilizing agents. Some so-called "sporicides" are known, but the possible applications thereof are limited, not only by effectiveness, but also by pH and speed of action, for example. Generally, spores need to be exposed to relatively high concentrations of sporicides for relatively long periods of time, e.g. from 15 to 60 minutes, in order to achieve a useful level of spore population reduction, i.e. a two or three logarithm reduction in viable count. A variety of compounds have been used to insure sterilization of spores and have found acceptance depending upon constraints imposed by environment and the required efficacy of action. Acids, alkali, phenols, iodophors, salts, heavy metals, chlorine, hypochlorite, alcohols, glutaraldehyde, formaldehyde, ethylene oxide, organic solvents and surfactants all have been shown to have some action as a sterilant. However, of these compounds only aldehydes, ethylene oxide, hypochlorites, and Alcide (EPA Reg. No. 456310-03), are commonly used commercially to kill spores.

Sterilization procedures are necessarily directed toward the destruction of ubiquitous microbes. Some bacterial spores are extremely resistant to heat and require heating in steam under pressure at greater than 120° C. for as long as eleven hours to insure destruction. Most spores are not this resistant, however, and are killed by moist heat at greater than 120° C. for thirty minutes. Bacterial spores are also very resistant to bactericidal compounds. For many commonly used disinfectants, such as hypochlorite and phenols, concentrations one-thousand to ten-thousand times greater are needed to kill spores than are needed to kill vegetative cells. An exception to this generalization is alkylating agents, such as ethylene oxide or formaldehyde, where one-half to fifteen times as much alkylating agent is needed to kill spores than is needed to kill vegetative cells. Therefore, a sporicidal agent that is capable of sterilizing a wide range of materials and surfaces in a simple and straight forward fashion is desirable.

Surprisingly, it has been found that spores are particularly sensitive to the method and compositions of the invention and that such formulations are generally stronger and faster than those hitherto available. The prior art is silent regarding the method and compositions of the instant invention.

OBJECTS OF THE INVENTION

It is an object of the present invention to provide a method effective for killing or rendering lifeless bacterial spores.

It is another object of the present invention to provide a composition effective for killing rapidly or rendering lifeless bacterial spores.

It is a further object of applicants' invention to provide a sterilant for a wide variety of hard surfaces such as metals, plastics, resins, rubbers, ceramics, and glasses.

A further object of the present invention is to provide a process for sterilizing various substrates.

It is also an object of applicants' invention to provide sterilizing compositions containing a spore germinant and a germicide.

It is a further object of applicants' invention to provide sterilizing compositions containing a an activator, a spore germinant and a germicide.

It is another object of applicants' invention to kill or render lifeless *Bacillus anthracis* spores.

Still a further object of applicants' invention is to provide an improved multi purpose liquid formulation for disinfecting and sterilizing hard surfaces.

It is yet a further objective of the present invention to provide a chemical disinfectant/sterilant which does not require an outside source of heat to be sporicidal.

Other objects of the present invention will be apparent to those skilled in the art.

The foregoing and other objects as defined herein are accomplished by the practice of this invention. The present invention is able to address many of the objectives discussed above.

SUMMARY OF THE INVENTION

The present invention is directed to a process for rendering bacterial endospores harmless and/or lifeless which method comprises the following steps: (a) adding an effective amount of a germinating agent to said endospores; and (b) adding an effective amount of a germicidal agent.

The instant invention is also directed to a method of killing spores comprising the steps of: (a) combining in an aqueous solution an effective amount of a germinating agent for said spores and an effective amount of a germicidal agent; and (b) contacting said spores with said aqueous solution therefore killing said spores.

Additionally, the present invention provides a method for sterilizing an aqueous solution to render such solution substantially free of spores which method comprises adding to said aqueous solution an effective amount of a germinating agent and an effective amount of a germicidal agent.

The invention also provides a method for sterilizing the surface of an article wherein the surface is at least substantially gas impermeable and said surface is contaminated with bacterial spores comprising the steps of exposing the spores on said surface to an effective amount of a germinating agent for said spores and an effective amount of a germicidal agent to sterilize said surface by killing the spores.

Furthermore, the invention provides a method of sterilizing objects or surfaces which comprise applying to objects or surfaces contaminated with *Bacillus anthracis* spores a sterilizing effective amount of a composition in aqueous solution containing an effective amount of a germinating agent and an effective amount of a germicide.

The invention also provides a method for sterilizing soils contaminated with bacterial spores comprising the steps of exposing the spores on said soils to an effective amount of a germinating agent for said spores and an effective amount of a germicidal agent to sterilize said soils by killing the spores.

The instant invention is also directed to a method for the disinfection and sterilization of material and surfaces contaminated with one or more members selected from the group consisting of bacteria and bacterial spores, comprising the steps of: (a) providing a biocidal fluid containing a mixture of effective amounts of a germinant and a germicide; and (b) contacting the material and surfaces contaminated with one or more members selected from the group consisting of bacteria and bacterial spores, with the biocidal fluid of step (a) for a time sufficient for disinfecting and sterilizing said material.

The invention further provides a sterilizing composition suitable for killing and rendering spores lifeless comprising: (a) an effective amount of a germinating agent; and (b) an effective amount of a germicide.

DESCRIPTION OF THE PREFERRED EMBODIMENTS

Within the context of the present specification, the term sterilization denotes the use of either physical or chemical agents to eliminate all viable microbes and spores from a material, while disinfection generally refers to the use of germicidal chemical agents to destroy the potential infectivity of a material.

It is well known that organisms in the genus Bacillus are aerobic rod shaped organisms which form resistant bodies called endospores when nutrients become limiting. One vegetative bacterial cell produces one endospore and one endospore, when conditions are right, produces one vegetative cell. Bacterial spores are dormant with no detectable metabolic activity and they can remain dormant for decades and possibly centuries. They are resistant to any chemical and physical agent that will harm the vegetative cell. It is also well known that bacterial endospores are extremely difficult to destroy. They are much more resistant to any chemical or physical agent than vegetative cells. Once these spores have contaminated an area or material it is almost impossible to completely remove 100% of the organisms by traditional means.

The traditional school of thought concerning the progression of a spore into a vegetative cell is that it is divided into three distinct sequential steps:

Step 1 is Activation. Activation is a process involving tertiary changes in the spore coat proteins such as breaking disulfide bonds. The most general mechanism for activating spores in the laboratory is heat shock: exposure to an elevated but sublethal temperature for a period of time. This type of activation is reversible by placing the spores at a lower temperature for some days. Chemicals, especially reducing agents that can break disulfide bonds, can act as activating agents (activators). In addition mild oxidizing agents and acids that result in a low pH can also activate spores.

A much slower activation (age activation) occurs upon storage of spores even at a lower temperature or under dry conditions; this activation is irreversible, as an increasing percentage of the spores being capable of germination increases as time progresses. The percentage of activated spores with age activation is usually quite low.

When activated spores are placed under favorable conditions, step 2, Germination, can take place. This process leads to the termination of the dormant stage of the spore. Germination is very rapid and is expressed by a loss of refractility and a loss of resistance of the spore to heat and other deleterious agents. Germination of activated spores requires a chemical trigger, a germinant. The specific substances which act as germinants are many and varied. They include glucose, adenine, L-alanine, calcium dipicolinate and various inorganic anions and cations. The particular germinant requirements often differ from species to species and maximal germination may require a combination of several germinants. The activity of the germinants are not additive but synergistic. If germination occurs in a medium which does not contain the nutrients required for vegetative growth no other changes will occur.

However, if nutrients required for growth are present upon germination the germinated spore will undergo step 3, outgrowth. Outgrowth involves an initial swelling of the spore within the spore coat accompanied by a rapid synthesis of a vegetative cell wall. The newly formed vegetative cell then emerges from the spore coat, elongates, and proceeds to undergo binary fission and reproduction.

Surprisingly, during the course of applicants' studies, it was discovered that when a new formulation of a chemical germinant combination is utilized, the endospores do not have an absolute requirement for the presence of activator chemicals. The combination of germinants may substitute for the activators. While activation of spores is not necessary if the correct combination of germinants are utilized it may still be added to speed up the germination process.

The present invention is directed to a process and product for the rapid decontamination of bacterial endospores in or on surfaces, buildings, structures, instruments, soil, water, and any other material. The process is such that the bacterial spore is converted to a vegetative cell by going through activation, germination and outgrowth and the product is a combination of chemicals that will force the endospore to convert to the vegetative cell.

The process of the present invention comprises the utilization of sublethal heat and/or chemicals known to act as a germinant to induce germination and outgrowth in the particular species of endospore-forming bacteria thus naturally converting the resistant endospores to much less resistant vegetative cells. By applying sublethal heat, applicant means subjecting the spores to a temperature range of about 65° C. to 75° C. more preferably 72° C.–75° C. In a preferred embodiment the spores are subjected to sublethal heat of 75° C. for about 12–20 minutes, preferably 14–17 minutes and most preferably 15–16 minutes.

The chemical germinants are applied to the surface or area contaminated with the endospores so that they come in contact with the endospore. The germinant solution can be applied in any manner but the preferred manner is by spraying as to produce a layer of the germinant solution that covers the surface. The germinant solution induces germination in a high percentage of the spores and the germinating spores release dipicolinic acid which acts as a additional germinant for any remaining spores. The preferred germinants are selected from the group consisting of glucose, adenine, L-alanine, calcium dipicolinate and various inorganic anions such as but not limited to chloride and borate and cations such as but not limited to $Na^+$, $Ca^{++}$, and $Mg^{++}$ as well as mixtures thereof.

A particular preferred solution contains 0.1% glucose , 4.0 mM adenosine, 4.0 mM L-alanine, 0.25% yeast extract, and 0.5% each of tryptone and peptone in distilled water.

After the addition of the germinant, the endospore undergoes the process of germination and the form of the organism is converted from a resistant endospore to a vegetative form. At this time, a germicidal chemical is sprayed on the same surface to kill all of the vegetative cells. This process of addition of activator-germinant followed by germicidal compound is repeated as many times as necessary until the concentration of the endospore producing bacterial species is completely reduced to a non detectable level.

The germicidal chemical may also be added to the chemical activator-germinant to kill the vegetative cell as it starts to emerge from the endospore.

An activating agent (activator) may also be added to the germinant solution. Also, a known quantity of Spores may be applied to the target surface in large quantities to be used as an indicator organism. Monitoring of the sterilization of the indicator organism will allow results to be quickly tested. In addition, by choosing a fast germinating organism dipicolinic acid can be released to speed up germination.

The process of the invention includes germinant chemicals specific for bacterial endospores and the application of the same. The application of the germinant solution induces rapid germination of the Bacillus endospores converting them into less resistant vegetative cells. Suprisingly, with the preferred germinant solution ,the addition of an activator chemical or chemicals is not necessary. A commercial germicide is included or added shortly afterward to kill the susceptible vegetative cells of the Bacillus. The process may be repeated until all the spores are all killed.

If an activator is desired, the preferred activator can be sublethal heat and/or thioglycollic acid, cysteine, glutathione, other sulfhydryl agents and even the growth medium thioglycollate broth.

The preferred germinant is a solution containing 0.1% glucose , 4.0 mM adenosine, 4.0 mM L-alanine, 0.25% yeast extract, and 0.5% each of tryptone and peptone. Suprisingly, with this germinant solution, the addition of an activator chemical or chemicals is not necessary.

Any chemical that induces activation-germination of bacterial endospores can be utilized. The following chemicals have been shown to be germinants for endospores: glucose, adenosine, inosine, L-alanine, Calcium dipicolinate, various inorganic cations and anions, and complex bacterial media such as peptone, tryptone, and yeast extract. Fluid thioglycollate growth medium, a broth containing thioglycollate, peptone and glucose can also be used with the activator-germinant solution.

The bactericidal chemical compound can be any compound known have germicidal properties and will kill vegetative cells bacteria.

The germicide which is useful in practicing the instant invention can be chosen from the any of following types of bactericides: (1) Phenol and phenolics such as o-phenylphenol and hexachlorophene; (2) Halogens such as Iodine and chlorine; (3) Alcohols such as ethanol and isopropanol; (4) Heavy metals such as silver, mercury, and copper solutions, (5) Surface active agents such as anionic surfactants; (6) Quaternary ammonium salts (quats); (7) organic acids; (8) aldehydes such as formaldehyde and glutaraldehyde; (9) gaseous chemosterilizers such as ethylene oxide and beta propiolactone; (10) oxidizing agents such as hydrogen peroxide and benzoyl peroxide.

Typical germicides which may be used in this invention include phenols; cresols; resorcinols; substituted phenols; aldehydes; benzoic acid; salicyclic acid; iodine; iodophors, such as betadine; chlorophors, such as hypochlorites; peroxides; such as hydrogen peroxide and zinc peroxide; heavy metals and their salts, such as merbromin, silver nitrate, zinc sulfate; surface-active agents, such as benzalkonium chloride; furan derivatives, such as nitrofurazone; sulfur and thiosulfates; salicylanilides; and carbanilides. Preferred germicides include betadine, iodine, silver nitrate and furan derivatives, such as nitrofurazone. Other germicides include parachloro meta xylenol, hexachlorophene, 2-bromo-2-nitropropane diol, salicylanilide, didecyl dimethyl ammonium chloride, cetyl dimethylethyl ammonium bromide, alkyl dimethyl benzyl ammonium chloride, alkyl dimethylethyl benzyl ammonium chloride, alkyl dimethylbenzyl ammonium succinate, alkyl dimethyl-3,4-dichlorobenzyl ammonium chloride, 3,3',4',5-tetra-chlorosalicylanilide, 3',4',5-trichlorosalicylanilide, 3,5-dibromo-3'-trifluoromethylsalicylanilide, 3,4,4'-trichlorocarb-amilide, benzalkonium chloride, chloramine, iodine, iodophors, chlorhexidine and salts thereof.

Other quaternary ammonium compounds of interest include quaternary salts containing either or both of aliphatic and aromatic moieties. Although quaternary ammonium salts are preferred, cationic phosphonium, or sulfonium, or any other positive nonmetallic nuclei may be selected. Some of the aliphatic or alicyclic substituents for the quaternary ions are alkyl groups containing one to 30 carbon atoms both linear and branched, alkoxy groups also containing one to 30 carbon atoms both linear and branched, alicyclic groups such as cyclohexyl and its alkylated or alkyloxylated derivatives, and halogenated alkyl, halogenated alicyclic, or halogenated alkyloxy derivatives.

Aromatic moieties, which may themselves be substituted by aliphatic, alicyclic, alkyloxy groups, useful as substituents for the quaternary cationic salts of the present invention are benzyl, tolyl, xylyl, naphthyl, pyridyl, benzal, quinolyl and the like. More specifically, some aliphatic quaternary ammonium salts which are useful in the present invention are: tetramethyl ammonium halide, trimethylethyl ammonium halide, dimethyldiethyl ammonium halide, methyltriethyl ammonium halide, tetraethyl ammonium halide, cetyidimethylethyl ammonium halide, trimethyin-propyl ammonium halide, dimethyldin-propyl ammonium halide, methyltrin-propyl ammonium halide, tetran-propyl ammonium halide, methylethyln-propyin-butyl ammonium halide, ethyln-propyinpentyl ammonium halide, trimethylallyl ammonium halide, dimethyldiallyl ammonium halide, methyltriallyl ammonium halide, tetraallyl ammonium halide, N,N,N,N',N',N'-hexaethyl-1,2-ethylene diammoniumhalide, N,N,N,N',N',N'-hexaethyl-1,4-butylenediammonium halide, N,N,N'-dibenzyl-N,N,N',N', tetramethyl-1,2-ethylene diammonium halide, N,N'-di(4-chlorobenzyl)-N,N,N',N'-tetramethyl-1,2-ethylenediammoniumhalide, N,N,N'-tetraethyl-N,n"-di-octadecyl-1,2-ethylene diammonium halide, N,N,N',N'-tetraethyl-N,N'-dihexadecyl-1,4-butylene diammonium halide, octadecyltrimethyl ammonium halide, dioctadecyldimethyl ammonium halide, trioctadecylmethyl ammonium halide tetraoctadecyl ammonium halide, hexadecyltriethyl ammonium halide, hexadecyidimethylethyl ammonium halide, hexadecyl-diethylmethyl ammonium halide, didecyidioctyl ammonium halide, didecyldihexyl ammonium halide, and hexyloctyldecyidodecyl ammonium halide.

Some representative useful quaternary ammonium salts containing an aromatic moiety include: benzylodecyldimethyl ammonium halide, o-tolyldodecyldimethyl ammonium halide, m-tolyldodecyldimethyl ammonium halide, p-tolyldodecyldimethyl ammonium halide, 2,3-xylyl-dodecyldimethyl ammonium halide, 2,4-xylydodecyldimethyl ammonium halide, 2,5-xylyl-dodecyldimethyl ammonium halide, 3,4-xylyldodecyldimethyl ammonium halide, 3,5-xylyl-dodecyldimethyl ammoniuim halide, 2-chlorobenzyldodecyldimethyl ammonium halide, 3-chloro-benzyldodecyldimethyl ammonium halide, 4-chlorobenzyldodecyldimethyl ammonium halide, 2,3-dichlorobenzyldodecyldimethyl ammonium halide, 2,4-dichlorobenzyldodecyldimethyl ammonium halide, 2,5-dichlorobenzyldodecyldimethyl ammonium halide, 2,6-dichlorobenzyl-dodecyldimethyl ammonium halide, 3,4-dichlorobenzyldodecyldimethyl ammonium halide, 3,5-dichlorobenzyldodecyldimethyl ammonium halide, 2-nitrobenzyldodecyldimethyl ammonium halide, 3-nitrobenzyldodecyldimethyl ammonium halide, 4-nitrobenzyldodecyldimethyl ammonium halide, 2,4-dinitrobenzyldodecyldimethyl ammonium halide, 3,5-dinitrobenzyldodecyldimethyl ammonium halide, 2-sulfobenzyldodecyldimethyl ammonium halide, 3-sulfobenzyldodecyldimethyl ammonium halide, 4-sulfobenzyldodecyldimethyl ammonium halide, 2-carboxybenzyldodecyldimethyl ammonium halide, 3-carboxybenzyl-dodecyldimethyl ammonium halide, 4-carboxybenzyldodecyldimethylammonium-halide, benzylhexyldimethyl ammonium halide, benzyloctyldimethyl ammonium halide, benzyldecyl-dimethyl ammonium halide, benzyldodecyldimethyl ammonium halide, benzyltetradecyldimethyl ammonium halide, benzylhexadecyldimethyl ammonium halide, benzyloctadecyldimethyl ammonium halide.

Some representative, useful quaternary ammonium salts containing heterocyclic, aromatic moieties include: n-hexylpyridinium halide, n-octylpyridinium halide, n-decylpyridinium halide, n-dodecylpyridinium halide, n-tetradecylpyridinium halide, n-hexadecylpyridinium halide, n-hexyllutidinium halide, n-octyllutidinium halide, n-decyllutidinium halide, n-dodecyllutidinium halide, n-tetradecyllutidinium halide, n-hexadecyllutidinium halide, n-hexylpicolinium halide, n-octylpicolinium halide, n-decylpicolinium halide, n-dodecylpicolinium halide, n-tetradecylpicolinium halide, n-hexadecylpicolinium halide, n-hexylquinolinium halide, n-octylquinolinium halide, n-decylquinolinium halide, n-dodecylquinolinium halide, n-tetradecylquinolinium halide, n-hexadecylquinolinium halide, n-hexylisoquinolinium halide, n-octylisoquinolinium halide, n-decylisoquinolinium halide, n-dodecylisoquinolinium halide, n-tetradecylisoquinolinium halide, n-hexadecylisoquinolinium halide, n-hexylquinazolinium halide, n-octylquinazolinium halide, n-decylquinazolinium halide, n-dodecylquinazolinium halide, n-tetradecylquinazolinium halide, n-hexadecylquinazolinium halide, n-hexylquinoxalinium halide, n-octylquinoxalinium halide, n-decylquinoxalinium halide, n-dodecylquinoxalinium halide, n-tetradecylquinoxalinium halide, n-hexadecylquinoxalinium halide, n-hexylpyridopyridinium halide, n-octylpyridopyridinium halide, n-decylpyridopyridinium halide, n-dodecylpyridopyridinium halide, n-tetradecylpyridopyridininum halide, and n-hexadecylpyridopyridinium halide.

The preferred counter ions for the quaternary cationic salts are halides, especially chloride and bromide. Particularly useful for practicing the present invention are alkyl-benzyldimethyl ammonium chlorides, wherein the alkyl groups contain between 10 and 18 carbon atoms, and cetyldimethylethyl ammonium bromide. The useful range of quaternary cationic salts in an effective amount of sterilant is from about 0.05% to 3% in actual use by weight.

Other counter ions, anions, useful in the practice of the present invention to neutralize the positive charge of the ammonium, phosphonium, sulfonium, or other positive moieties can be found in the following list bicarbonate, bisulfite, fluoride, borate, carbonate, nitrite, nitrate, phosphite, phosphate, sulfite, sulfate, chloride, hypochlorite, chlorite, chlorate, perchlorate, hydroxide, fluoborate, iodide, iodate, periodate, and bromate.

The germicide solution typically contains an effective amount of a germicide, typically 0.01% to 10% by weight, surfactants 0.1% to 0.5% by weight, and the balance are inert ingredients such as solvents preferably water. Other solvents include water miscible alcohols such as ethanol and isopropanol.

The compositions of the invention which include the germicides advantageously contain surfactants, for example anionic compounds such as soaps and other carboxylates (e.g. alkali metal salts of higher fatty acids), derivatives of sulfuroxyacids (e.g. sodium salt of dodecylbenzenesulfonic acid, watersoluble salts of sulfuric acid monoesters of higher molecular alcohols or of their polyglycol ethers, for example soluble salts of dodecyl alcohol sulfate or of dodecyl alcohol polyglycol ether sulfate), derivatives of phosphorus-oxyacids (e.g. phosphates), derivatives with acid (electrophilic) nitrogen in the hydrophilic group (e.g. disulfine salts), cationic surfactants, such as amines and their salts (e.g. lauryldiethylenetriamine), onium compounds, amine oxides or nonionic surfactants, e.g. polyhydroxy compounds, surfactants based on mono- or polysaccharides, higher molecular acetylene glycols, polyglycol ethers (e.g. polyglycol ethers of higher fatty alcohols, polyglycol ethers of higher molecular alkylated phenols). The preferred surfactants are water soluble non-ionic surfactants.

The water soluble nonionic surfactants utilized in this invention are commercially well known and include the primary aliphatic alcohol ethoxylates, secondary aliphatic alcohol ethoxylates, alkylphenol ethoxylates and ethylene-oxide-propylene oxide condensates on primary alkanols, such a Plurafacs (BASF) and condensates of ethylene oxide with sorbitan fatty acid esters such as the Tweens (ICI). The nonionic synthetic organic detergents generally are the condensation products of an organic aliphatic or alkyl aromatic hydrophobic compound and hydrophilic ethylene oxide groups. Practically any hydrophobic compound having a carboxy, hydroxy, amido, or amino group with a free hydrogen attached to the nitrogen can be condensed with ethylene oxide or with the polyhydration product thereof, polyethylene glycol, to form a water-soluble nonionic detergent. Further, the length of the polyethenoxy chain can be adjusted to achieve the desired balance between the hydrophobic and hydrophilic elements.

The nonionic detergent class includes the condensation products of a higher alcohol (e.g., an alkanol containing about 8 to 18 carbon atoms in a straight or branched chain configuration) condensed with about 5 to 30 moles of ethylene oxide, for example, lauryl or myristyl alcohol condensed with about 16 moles of ethylene oxide (EO), tridecanol condensed with about 6 to moles of EO, myristyl alcohol condensed with about 10 moles of EO per mole of myristyl alcohol, the condensation product of EO with a cut of coconut fatty alcohol containing a mixture of fatty alcohols with alkyl chains varying from 10 to about 14 carbon atoms in length and wherein the condensate contains either about 6 moles of EO per mole of total alcohol or about 9 moles of EO per mole of alcohol and tallow alcohol ethoxylates containing 6 EO to 11 EO per mole of alcohol.

A preferred group of the foregoing nonionic surfactants are the Neodol ethoxylates (Shell Co.), which are higher aliphatic, primary alcohol containing about 9–15 carbon atoms, such as $C_9$–$C_{11}$ alkanol condensed with 2.5 TO 10 moles of ethylene oxide (NEODOL 91-2.5 OR -5 OR -6 OR -8), $C_{12}$–$C_{13}$ alkanol condensed with 6.5 moles ethylene oxide (Neodol 23-6.5), $C_{12}$–$C_{15}$ alkanol condensed with 12 moles ethylene oxide (Neodol 25-12), $C_{14}$–$C_{15}$ alkanol condensed with 13 moles ethylene oxide (Neodol 45-13), and the like.

Additional satisfactory water soluble alcohol ethylene oxide condensates are the condensation products of a secondary aliphatic alcohol containing 8 to 18 carbon atoms in a straight or branched chain configuration condensed with 5 to 30 moles of ethylene oxide. Examples of commercially available nonionic detergents of the foregoing type are $C_{11}$–$C_{15}$ secondary alkanol condensed with either 9 EO (Tergitol 15-S-9) or 12 EO (Tergitol 15-S-12) marketed by Union Carbide.

Other suitable nonionic detergents include the polyethylene oxide condensates of one mole of alkyl phenol containing from about 8 to 18 carbon atoms in a straight- or branched chain alkyl group with about 5 to 30 moles of ethylene oxide. Specific examples of alkyl phenol ethoxylates include nonyl phenol condensed with about 9.5 moles of EO per mole of nonyl phenol, dinonyl phenol condensed with about 12 moles of EO per mole of phenol, dinonyl phenol condensed with about 15 moles of EO per mole of phenol and di-isoctylphenol condensed with about 15 moles of EO per mole of phenol. Commercially available nonionic surfactants of this type include Igepal CO-630 (nonyl phenol ethoxylate) marketed by GAF Corporation.

Also among the satisfactory nonionic detergents are the water-soluble condensation products of a $C_8$–$C_{20}$ alkanol with a heteric mixture of ethylene oxide and propylene oxide wherein the weight ratio of ethylene oxide to propylene oxide is from 2.5:1 to 4:1, preferably 2.8:1 to 3.3:1, with the total of the ethylene oxide and propylene oxide (including the terminal ethanol or propanol group) being from 60–85%, preferably 70–80%, by weight. Such detergents are commercially available from BASF-Wyandotte and a particularly preferred detergent is a $C_{10}$–$C_{16}$ alkanol condensate with ethylene oxide and propylene oxide, the weight ratio of ethylene oxide to propylene oxide being 3:1 and the total alkoxy content being about 75% by weight.

Condensates of 2 to 30 moles of ethylene oxide with sorbitan mono- and tri-$C_{10}$–$C_{20}$ alkanoic acid esters having a HLB of 8 to 15 also may be employed as the nonionic detergent ingredient in the described composition. These surfactants are well known and are available from Imperial Chemical Industries under the Tween trade name. Suitable surfactants include polyoxyethylene (4) sorbitan monolaurate, polyoxyethylene (4) sorbitan monostearate, polyoxyethylene (20) sorbitan trioleate and polyoxyethylene (20) sorbitan tristearate.

Other suitable water-soluble nonionic detergents are marketed under the trade name "Pluronics". The compounds are formed by condensing ethylene oxide with a hydrophobic base formed by the condensation of propylene oxide with propylene glycol. The molecular weight of the hydrophobic portion of the molecule is of the order of 950 to 4000 and preferably 200 to 2,500. The addition of polyoxyethylene radicals to the hydrophobic portion tends to increase the solubility of the molecule as a whole so as to make the surfactant water-soluble. The molecular weight of the block polymers varies from 1,000 to 15,000 and the polyethylene oxide content may comprise 20% to 80% by weight. Preferably, these surfactants will be in liquid form and satisfactory surfactants are available as grades L 62 and L 64.

This invention can be applied to surfaces, equipment, soil, or liquids contaminated with *Bacillus anthracis* or other aerobic or anaerobic pathogenic spore-forming bacteria. It can be utilized to remove bacterial spores from *Bacillus thuringiensis* formulations.

EXAMPLES

Example 1

Spore Suspension:

*Bacillus cereus* (or *Bacillus anthracis*) is grown on nutrient agar plates at 28° C. until the culture sporulates. The endospores are harvested and added to a 10% solution of ethanol. A viable spore count is conducted by tube dilution or plate counts. The concentration of the spore suspension is set at 1×108 per ml. *Bacillus cereus* spore suspension is prepared in the same manner.

Example 2
Heat Activated Spore Suspension

Twenty ml. of the spore supension is heated to 75 C for 15 minutes.

Example 3

Activating agents: (1) Thioglycollic acid (3 ml per liter) or (2) sublethal heat (75° C. for 15 minutes.)

Germinant solution: a solution containing 0.1% glucose 4.0 mM adenosine, 4.0 mM L-alanine, 0.25% yeast extract, and 0.5% each of tryptone and peptone in distilled water.

Germicide solution is n-alkyl(50% $C_{14}$, 40% $C_{12}$, 10% $C_{16}$)dimethyl benzylammonium chloride 0.8%, surfactants 0.25%, AND inert ingredients, 98.95%

Example 4
Test Tube Method With Heat Activated Spores

One ml of the heat activated Bacillus spore suspension is added to each of six test tubes: The following additions are made to selected tubes:

tube #
1. 8 ml distilled water
2–7 8 ml of germinant solution 1 ml of germicide is added to tube #1 and 2. The process is repeated with tubes 3–7 at 1,4,8,12, and 24 hours respectively. The tubes are incubated at room temperature for 24 hours and viable counts are made on each tube to determine the viable spores and the percentage of inactivation.

Example 5
Test Tube Method With Chemical Activator

One ml of a Bacillus spore suspension is added to each of six test tubes:

The following additions are made to selected tubes:
tube#
1 9 ml distilled water
2–7 1 ml activating agent+7 ml of germinant solution 1 ml of germicide is added to tube #1 and 2. The process is repeated with tubes 3–6 at 1,4,8,12, and 24 hours respectively. The tubes are incubated at room temperature for 24 hours and viable counts are made on each tube to determine the viable spores and the percentage of inactivation.

Example 6
Surface Test Method:

One ml of the Bacillus spore suspension is spread evenly over the bottom surface of nine petri dishes and allowed to dry.

The following solutions are sprayed on the selected petri dishes:

Petri Dish #
1 distilled water
2–7 activating agent+germinant solution

At 0, 1,4,8,12, and 24 hours, germicide solution is sprayed on each petri dish respectively(1–7). The petri dishes are incubated at room temperature for 24 hours. Ten ml of nutrient broth is added to each petri dish and the liquid material is transferred to a sterile test tube with spore/cell suspension. Viable counts are made on each spore/cell suspension to determine the viable spores and the percentage of inactivation is calculated. The activating agent can be added in advance of the germinant solution if desired.

Various changes and modifications may be made within the purview of this invention, as will be readily apparent to those skilled in the art. Such changes and modifications are within the scope and teachings of this invention as defined by the claims appended hereto. The invention is not to be limited by the examples given herein for purposes of illustration, but only by the scope of the appended claims and their equivalents.

What I claim is:

1. A process for rendering bacterial endospores harmless and/or lifeless which method comprises the following steps:
    (a) adding an effective amount of a germinating agent to said endospores;
    (b) adding an effective amount of a germicidal agent; and
    (c) providing sublethal heat and/or adding a chemical activating agent.

2. The process of claim 1 wherein said germinating agent is selected from the group consisting of glucose, adenosine, L-alanine, yeast extract, tryptone, peptone and mixtures thereof.

3. The process of claim 1 wherein said germicide is a phenol.

4. The process of claim 1 wherein said germicide is a quaternary ammonium salt.

5. The process of claim 4 wherein said quaternary ammonium salt is n-alkyl(50% $C_{14}$, 40% $C_{12}$, 10% $C_{16}$)dimethyl benzylammonium chloride.

6. A method of killing spores comprising the steps of: (a) combining in an aqueous solution an effective amount of a germinating agent for said spores and an effective amount of a germicidal agent; and (b) contacting said spores with said aqueous solution therefore killing said spores; said germinating agent containing 0.1% glucose, 4.0 mM adenosine, 4.0 mM L-alanine, 0.25% yeast extract, and 0.5% each of tryptone and peptone in distilled water.

7. A method for sterilizing an aqueous solution to render such solution substantially free of spores which method comprises adding to said aqueous solution an effective amount of a germinating agent and an effective amount of a germicidal agent, said germinating agent containing 0.1% glucose, 4.0 mM adenosine, 4.0 mM L-alanine, 0.25% yeast extract, and 0.5% each of tryptone and peptone in distilled water.

8. A method for sterilizing the surface of an article wherein the surface is at least substantially gas impermeable and said surface is contaminated with bacterial spores comprising the steps of exposing the spores on said surface to an effective amount of a germinating agent for said spores and an effective amount of a germicidal agent to sterilize said sure by killing the spores, said germinating agent containing 0.1% glucose, 4.0 mM adenosine, 4.0 mM L-alanine, 0.25% yeast extract, and 0.5% each of tryptone and peptone in distilled water.

9. A method for sterilizing soils contaminated with bacterial spores comprising the steps of exposing the spores on said soils to an effective amount of a germinating agent for said spores and an effective amount of a germicidal agent to sterilize said soils by killing the spores, said germinating agent containing 0.1% glucose, 4.0 mM adenosine, 4.0 mM L-alanine, 0.25% yeast extract, and 0.5% each of tryptone and peptone in distilled water.

10. A method of sterilizing objects or surfaces which comprise applying to objects or surfaces contaminated with *Bacillus anthracis* spores a sterilizing effective amount of a composition in aqueous solution containing an effective amount of a germinating agent and an effective amount of a germicide, said germinating agent containing 0.1% glucose, 4.0 mM adenosine, 4.0 mM L-alanine, 0.25% yeast extract, and 0.5% each of tryptone and peptone in distilled water.

11. A method for the disinfection and sterilization of material and surfaces contaminated with one or more members selected from the group consisting of bacteria and bacterial spores, comprising the steps of:

(a) providing a biocidal fluid containing a mixture of effective amounts of a germinant and a germicide; said germinant containing 0.1% glucose, 4.0 mM adenosine, 4.0 mM L-alanine, 0.25% yeast extract, and 0.5% each of tryptone and peptone in distilled water; and (b) contacting the material and surfaces contaminated with one or more members selected from the group consisting of bacteria and bacterial spores, with the biocidal fluid of step (a) for a time sufficient for disinfecting and sterilizing said material.

12. A sterilizing composition suitable for killing and rendering spores lifeless comprising:

(a) an effective amount of a germinating agent, said germinating agent containing 0.1% glucose, 4.0 mM adenosine, 4.0 mM L-alanine, 0.25% yeast extract, and 0.5% each of tryptone and peptone in distilled water; and (b) an effective amount of a germicide.

13. The sterilizing composition of claim 12 wherein said germicide is selected from the group consisting of: (1) Phenolics; (2) Halogens; (3) Alcohols; (4) Heavy metals; (5) Surface active anionic surfactants; (6) Quaternary ammonium salts; (7) organic acids; (8) aldehydes; (9) gaseous chemosterilizers; (10) and oxidizing agents.

14. The sterilizing composition of claim 12 further comprising a surfactant.

15. The sterilizing composition of claim 12 wherein said surfactant is a non-ionic surfactant.

* * * * *